United States Patent [19]

Tosaka et al.

[11] 4,368,266

[45] Jan. 11, 1983

[54] METHOD FOR PRODUCING L-GLUTAMIC ACID BY FERMENTATION

[75] Inventors: Osamu Tosaka, Tokyo; Yutaka Murakami, Yokosuka; Shigeho Ikeda; Hiroe Yoshii, both of Yokohama, all of Japan

[73] Assignee: Ajinomoto Company Incorporated, Tokyo, Japan

[21] Appl. No.: 218,071

[22] Filed: Dec. 19, 1980

[30] Foreign Application Priority Data

Dec. 27, 1979 [JP] Japan ................................. 54-170927
Jul. 10, 1980 [JP] Japan ................................. 55-94395

[51] Int. Cl.³ ........................ C12P 13/14; C12N 1/20; C12R 1/13; C12R 1/15
[52] U.S. Cl. ................................... 435/110; 435/253; 435/840; 435/843
[58] Field of Search ................ 435/110, 253, 840, 843

[56] References Cited

U.S. PATENT DOCUMENTS 3,709,787  1/1973  Kanagaki et al. ................... 435/110
3,939,042  2/1976  Nakayama et al. ................. 435/110

FOREIGN PATENT DOCUMENTS 56-8694  1/1981  Japan .................................. 435/849

*Primary Examiner*—Robert J. Warden
*Attorney, Agent, or Firm*—Oblon, Fisher, Spivak, McClelland & Maier

[57] ABSTRACT

Mutants of the genus Brevibacterium or Corynebacterium requiring acetic acid for growth produce L-glutamic acid in an improved yield, especially when they are cultured in an aqueous culture medium containing both saccharide and aliphatic alcohol or acid as the carbon source.

11 Claims, No Drawings

METHOD FOR PRODUCING L-GLUTAMIC ACID BY FERMENTATION

FIELD OF THE INVENTION

This invention relates to a method for producing L-glutamic acid by fermentation

DESCRIPTION OF THE PRIOR ART

L-Glutamic acid has been produced by fermentation using a microorganism of the genus Brevibacterium or Corynebacterium. Various attempts have been done to improve the productivity of the known glutamic acid producing strains by artificial mutation techniques. Examples of such artificial mutants are mutants of Brevibacterium resistant to S-2-amino-ethyl-cysteine (Japanese Published Unexamined Patent Application No. 126877/1975, mutants of Brevibacterium and Corynebacterium resistant to fluorocitric acid, ketomalonic acid, α-amino-β-hydroxyvaleric acid, DL-threoninehydroxamate, 2-amino-3-phosphopropionic acid or 5-aminolevulinic acid (Japanese Published Unexamined Patent Application No. 89045/1979), mutants of Brevibacterium and Corynebacterium sensitive to lysozyme (Japanese Published Unexamined Patent Application No. 122794/1979), mutants of Brevibacterium and Corynebacterium having reduced activity of pyruvic acid dehydrogenase (Japanese Published Unexamined Patent Application No. 21762/1980), mutants resistant to glutamic acid or glutamic acid-analogue of Brevibacterium or Corynebacterium (Japanese Published Unexamined Patent Application No. 21763/1980), and mutants of Brevibacterium resistant to 2,6-pyridine-dicarboxylic acid (Japanese Published Unexamined Patent Application No. 21764/1980).

SUMMARY OF THE INVENTION

It has now found that mutants of the genus Brevibacterium or Corynebacterium requiring acetic acid for growth produce L-glutamic acid in an improved yield, especially when they are cultured in an aqueous culture medium containing both saccharide and aliphatic alcohol or acid as the carbon source.

Now, it is provided a method for producing L-glutamic acid which comprises culturing in an aqueous culture medium a mutant of the genus Brevibacterium or Corynebacterium which requires acetic acid for growth, and recovering L-glutamic acid accumulated in the resulted culture liquid.

DESCRIPTION OF THE PREFERRED EMBODIMENTS

The mutants employed in this invention belong to the genus Brevibacterium or Corynebacterium, and require acetic acid for growth. Examples of such mutants are:

Brevibacterium lactofermentum AJ 11515 (FERM-P 5335, NRRLB-12308)
Brevibacterium lactofermentum AJ 11516 (FERM-P 5336, NRRLB-12309)
Brevibacterium flavum AJ 11517 (FERM-P 5337, NRRLB-12310)
Corynebacterium acetoacidphilum AJ 11601 (FERM-P 5626, NRRLB-12311)
Corynebacterium acetoacidsphilum AJ 11602 (FERM-P 5627, NRRLB-12312)
Corynebacterium glutamicum AJ 11603 (FERM-P 5628, NRRLB-12313).

AJ 11516 and AJ 11602 are additionally deficient in isocitrate-lyase.

The mutants examplified above were derived from the parent strains of Brevibacterium lactofermentum ATCC 13869, Brevibacterium flavum ATCC 14067, Corynebacterium acetoacidsphilum ATCC 13870 and Corynebacterium glutamicum ATCC 13032, respectively.

The mutants of this invention can be induced by conventional manner, such as irradiation of cells to UV-rights or X-rays, and exposure of cells to a mutagen (such as N-methyl-N'-nitro-N-nitroso-guanidine), from the parent strains mentioned above and other glutamic acid producing bacteria belonging to the genus Brevibacterium or Corynebacterium. Other examples of glutamic acid producing bacteria used as the parent strain are:

Brevibacterium saccharolyticum ATCC 14066,
Brevibacterium divaricatum ATCC 14020,
Corynebacterium callunae ATCC 15991 and
Corynebacterium lilium ATCC 15990.

Growth of the mutants of this invention and their parents in a medium containing acetic acid as the sole carbon source is shown in Table 1.

The experiment was carried out as follows:

An aqueous medium was prepared to contain 0.5 g/dl glucose, 0.15 g/dl urea, 0.15 g/dl $(NH_4)_2SO_4$, 0.3 g/dl $KH_2PO_4$, 0.1 g/dl $K_2HPO_4$, 0.01 g/dl $MgSO_4.7H_2O$, 0.1 mg/dl $CaCl_2.2H_2O$, 10 μg/dl thiamine.HCl, 3 μg/dl biotin, 0.44 mg/dl $Na_2B_4O_7.10H_2O$, 4.85 mg/dl $FeCl_2.6H_2O$, 1.95 mg/dl $CuSO_4.5H_2O$, 0.185 mg/dl $Mo_7O_{24}.4H_2O$, 44 mg/dl $ZnSO_4.7H_2O$, 0.36 mg/dl $MnCl_2.4H_2O$ and the amount of acetic acid shown in Table 1, and the pH was adjusted to 7.0. Tested microorganisms previously cultured at 31.5° C. for 24 hours in a medium of pH 7.0 containing 1 g/dl peptone, 1 g/dl yeast extract and 0.5 g/dl NaCl were inoculated into 3 ml batches of the aqueous medium placed in test tubes after having suspended in sterilized water.

Growth was determined after 24 hours aerobical cultivation at 31.5° C., by measuring optical density at 562 mμ of the resulting culture broths.

TABLE 1

| | | Growth (Optical density) Acetic acid concentration | | | | |
|---|---|---|---|---|---|---|
| | | 0 | 0.03 | 0.06 | 0.4 | 0.5 |
| ATCC | 13869 | 1.02 | 1.04 | 1.02 | 1.02 | 1.04 |
| AJ | 11515 | 0 | 0.30 | 0.45 | 0.90 | 1.00 |
| AJ | 11516 | 0 | 0.29 | 0.40 | 0.95 | 1.02 |
| ATCC | 14067 | 1.08 | 1.08 | 1.08 | 1.08 | 1.08 |
| AJ | 11517 | 0.05 | 0.25 | 0.60 | 0.88 | 1.08 |
| ATCC | 13870 | 1.05 | 1.05 | 1.08 | 1.07 | 1.08 |
| AJ | 11601 | 0 | 0.25 | 0.40 | 0.92 | 1.06 |
| AJ | 11602 | 0 | 0.20 | 0.38 | 0.90 | 1.07 |
| ATCC | 13032 | 1.06 | 1.05 | 1.07 | 1.08 | 1.08 |
| AJ | 11603 | 0 | 0.28 | 0.52 | 0.95 | 1.08 |

Isocitrate-lyase activity was determined as to the mutants deficient in isocitrate-lyase and their parents, and the results are shown in Table 2.

TABLE 2

| Strain tested | | Specific activity ΔE/mg-protein | Relative activity (%) |
|---|---|---|---|
| ATCC | 13869 | 18.4 | 100 |
| AJ | 11516 | 0 | 0 |
| ATCC | 13870 | 23.0 | 100 |

TABLE 2-continued

| Strain tested | Specific activity ΔE/mg-protein | Relative activity (%) |
|---|---|---|
| AJ 11602 | 0 | 0 |

The determination of isocitrate-lyase activity was carried out as follows:

A medium of pH 7.0 containing 2.5 g/dl glucose, 0.8 g/dl ammonium acetate, 0.1 g/dl $KH_2PO_4$, 0.1 g/dl $MgSO_4.7H_2O$, 1 mg/dl $MnSO_4.4H_2O$, 0.4 g/dl urea, 0.3 μg/dl biotin, 20 μg/dl thiamine. HCl and 48 mg/dl (as total nitrogen) soybean protein acidhydrolysate, 20 ml of the medium was placed in 500 ml shaking flask, and heated to sterilize. Tested strain was inoculated into the medium and cultured at 31.5° C. with shaking until early exponential growth phase (10~16 hours cultivation time). Cells were separated, washed and exposed to supersonic waves. Protein fraction was separated with "Sephadex G-10" as a enzyme preparation.

Isocitrate-lyase activity was determined as to the enzyme preparation following the method shown in "Journal of Biochemistry" 49, 262 (1961).

The media used for the cultivation mentioned above are conventional themselves except that they contain a nutrient for satisfying acetic acid requirement, and contain carbon source, nitrogen source, inorganic ions, and when required minor organic nutrient. Nutrients for satisfying the acetic acid-requirement are aliphatic acid such as acetic acid, propionic acid, palmitic acid and stearic acid, and aliphatic alcohol such as ethanol and propanol.

The nutrient for satisfying acetic acid-requirement can be used also as the carbon source. The best result can be obtained when the nutrient for satisfying acetic acid-requirement is used as the carbon source together with saacharide such as glucose, fructose and sucrose, and raw material including the saccharide (such as starch hydrolysate, cellulose hydrolysate, fruit juice, cane molasses, beet molasses and soy-whey).

When saccharide and aliphatic alcohol or acid are used together with the carbon source, they are added to the medium in the ratio of 3 to 2 weight of saccharide to 2 to 1 weight of aliphatic alcohol or acid.

As the nitrogen sources, conventional sources such as ammonium salts, aqueous ammonia, gaseous ammonia and urea are used. When required, inorganic ions such as phosphate ions and magnesium ions are supplemented. Minor organic nutrients such as thiamine and biotin are added to the medium if the medium contain them deficiently. When the medium contain excessive amount of biotin, biotin-suppressing agent such as polyoxyethylene-sorbitane-monopalmitate and penicillin are used in the conventional manner.

Cultivation is carried out under an aerobic condition. Suitable cultivation temperature and pH are from 27° to 37° C. and from 6 to 9, respectively.

The L-glutamic acid thus accumulated in the culture medium can be recovered by known methods.

EXAMPLE 1

An aqueous medium containing 2.3 g/dl glucose, 1 g/dl ammonium acetate, 1 g/dl sodium acetate, 0.1 g/dl, $KH_2PO_4$, 0.1 g/dl $MgSO_4.7H_2O$, 20 μg/dl thiamine.HCl, 0.6 g/dl urea, 1 mg/dl $FeSO_4.7H_2O$, 1 mg/dl $MnSO_4.4H_2O$, 36 mg (as total nitrogen)/dl soybean protein-acid-hydrolysate and 2 μg/l biotin was prepared, adjusted to pH 7.0, and 20 ml batches of the aqueous medium were placed in 500 ml shaking flasks, and sterilized at 115° C. for 10 minutes. The microorganisms listed in Table 3 were inoculated into the media and cultured at 31.5° C. with shaking. During the cultivation, the pH was adjusted with 45 g/dl urea and 2N $H_2SO_4$ at pH 6.5 to 8.0.

The cultivation was discontinued at 36 hours cultivation, and the yield of L-glutamic acid accumulated in the medium was calculated. The results are shown in Table 3.

TABLE 3

| Microorganism tested | Yield of L-glutamic acid (%) |
|---|---|
| ATCC 13870 | 47% |
| AJ 11601 | 56 |
| AJ 11602 | 61 |
| ATCC 13032 | 45 |
| AJ 11603 | 57 |
| ATCC 13869 | 46 |
| AJ 11515 | 57 |
| AJ 11516 | 61 |
| ATCC 14067 | 44 |
| AJ 11517 | 56 |

The yield of L-glutamic acid is the ratio of the amount of L-glutamic acid produced in the culture medium to the amount of carbon source(s) used.

EXAMPLE 2

An aqueous medium was prepared to contain 5.6 g (as sugar)/dl cane molasses, 1.4 g/dl acetic acid, 0.2 g/dl $KH_2PO_4$, 0.1 g/dl $MgSO_4.7H_2O$, 0.05 g/dl ammonium sulfate, 1 mg/dl $MnSO_4.4H_2O$, 1 mg/dl $FeSO_4.7H_2O$, 3 μg/l biotin, 36 mg (as total-nitrogen) soybean protein acid-hydrolysate and 200 μg/l thiamine.HCl, and 300 ml batches of the aqueous medium were placed in 1.5 l fermenters and heated at 120° C. for 15 minutes to sterilize.

The microorganisms listed in Table 4 previously cultured were inoculated into the media and cultured at 31.5° C. maintaining the pH at 7.8 under an aerobic condition.

When optical density at 562 nm of 26 times dilute of the medium reached 0.3, polyoxyethylene-sorbitane-monopalmitate was added to contain 0.2 g/dl in the medium. Acetic acid concentration in the medium was maintained in the range from 0.1 to 0.5 g/dl by feeding to the medium a feeding solution containing 17 g (as sugar) /dl cane molasses, 15 g (as acetic acid) /dl ammonium acetate, 15 g/dl acetic acid and 13 g (as acetic acid) /dl sodium acetate.

When the cultivation was continued for 48 hours, L-glutamic acid was obtained in the yield shown in Table 4.

TABLE 4

| Microorganism tested | Yield of L-glutamic acid (%) |
|---|---|
| ATCC 13870 | 48 |
| AJ 11602 | 62 |
| ATCC 13869 | 47 |
| AJ 11516 | 62 |

EXAMPLE 3

An aqueous medium containing 1 g/dl glucose, 0.5 g/dl ethanol, 0.1 g/dl $KH_2PO_4$, 0.1 g/dl $MgSO_4.7H_2O$, 1 mg/dl $MnSO_4.4H_2O$, 1 mg/dl $FeSO_4.7H_2O$, 3 μg/l biotin, 1.0 g/dl ammonium sulfate, 96 mg (as total nitrogen)/dl soybean protein-acid-hydrolysate, and 200 μg/l thiamine.HCl, and 30 ml batches of the aqueous medium were placed in 500 ml shaking flasks and heated at 115° C. for 10 minutes to sterilize.

The microorganisms listed in Table 5 were cultured in the medium at 31.5° C. with shaking. During the cultivation, 4.2 g of a feeding solution containing 30 g/dl glucose, 15 g/dl ethanol and 15 g/dl ammonium sulfate were added to the medium, when the ethanol concentration in the medium become below 0.5 g/dl. The additions were done twice. The cultivations were discontinued at 36 hours cultivation from the initiation. The results are shown in Table 5.

TABLE 5

| Microorganism tested | | Yield of L-glutamic acid (%) |
|---|---|---|
| ATCC | 13869 | 53 |
| AJ | 11516 | 63 |
| ATCC | 13870 | 52 |
| AJ | 11602 | 63 |

What is claimed as new and intended to be covered by Letters Patent is:

1. A method for producing L-glutamic acid by fermentation which comprises aerobically culturing an L-glutamic acid producing mutant of the genus Brevibacterium or Corynebacterium which is deficient in isocitrate lyase and requires acetic acid for growth, and recovering L-glutamic acid accumulated in the resulting culture liquid.

2. The method of claim 1, wherein said aqueous medium contains as the carbon source both saccharide and aliphatic alcohol or acid.

3. The method of claim 2, wherein said saccharide is glucose, fructose or sucrose and crude material containing the saccharide.

4. The method of claim 3, wherein said crude material is starch hydrolysate, cane molasses or beet molasses.

5. The method of claim 2, wherein said aliphatic alcohol is ethanol or propanol.

6. The method of claim 2, wherein said aliphatic acid is acetic acid, propionic acid, palmitic acid or stearic acid.

7. The method of claim 1 or 2, wherein said aqueous culture medium contains acetic acid and starch hydrolysate as the carbon source.

8. The method of claim 1 or 2 wherein said aqueous culture medium contains acetic acid and beet molasses.

9. The method of claim 1 or 2, wherein said aqueous culture medium contains acetic acid and cane molasses.

10. The method of claim 1, wherein said saccharide and aliphatic alcohol or acid are used as the carbon source in the ratio of 3 to 2 weight of saccharide to 2 to 1 weight of aliphatic alcohol or acid.

11. A biological pure culture of an L-glutamic acid producing mutant of the genus Brevibacterium or Corynebacterium which is deficient in isocitrate lyase and requires acetic acid for growth.

* * * * *